United States Patent
Lightcap et al.

(10) Patent No.: US 10,932,970 B2
(45) Date of Patent: Mar. 2, 2021

(54) SYSTEMS AND METHODS FOR MONITORING AND CONTROLLING BED FUNCTIONS

(71) Applicant: CareView Communications, Inc., Lewisville, TX (US)

(72) Inventors: Jeffrey C. Lightcap, Charleston, SC (US); Steven Gail Johnson, Highland Village, TX (US); Derek del Carpio, Corinth, TX (US)

(73) Assignee: CareView Communications, Inc., Lewisville, TX (US)

( * ) Notice: Subject to any disclaimer, the term of this patent is extended or adjusted under 35 U.S.C. 154(b) by 0 days.

(21) Appl. No.: 16/542,409

(22) Filed: Aug. 16, 2019

(65) Prior Publication Data
US 2020/0060910 A1    Feb. 27, 2020

Related U.S. Application Data

(60) Provisional application No. 62/723,193, filed on Aug. 27, 2018.

(51) Int. Cl.
| | |
|---|---|
| *A61G 7/05* | (2006.01) |
| *G06T 7/20* | (2017.01) |
| *G06T 7/70* | (2017.01) |
| *G06T 7/00* | (2017.01) |
| *G05B 15/02* | (2006.01) |
| *A61G 7/018* | (2006.01) |
| *G08B 21/02* | (2006.01) |
| *A61B 5/00* | (2006.01) |
| *A61B 5/11* | (2006.01) |

(Continued)

(52) U.S. Cl.
CPC ............ *A61G 7/052* (2016.11); *A61B 5/1114* (2013.01); *A61B 5/1128* (2013.01); *A61B 5/447* (2013.01); *A61G 7/005* (2013.01); *A61G 7/018* (2013.01); *A61G 7/0516* (2016.11); *A61G 7/0573* (2013.01); *A61G 7/05769* (2013.01); *G05B 15/02* (2013.01); *G06T 7/0012* (2013.01); *G06T 7/20* (2013.01); *G06T 7/70* (2017.01); *G08B 3/10* (2013.01); *G16H 40/63* (2018.01); *H04N 5/33* (2013.01); *H04N 7/183* (2013.01); *A61G 2203/40* (2013.01); *A61G 2203/46* (2013.01); *G06T 2207/10028* (2013.01); *G06T 2207/10048* (2013.01); *G06T 2207/30196* (2013.01); *G06T 2207/30232* (2013.01); *G08B 21/02* (2013.01)

(58) Field of Classification Search
None
See application file for complete search history.

(56) References Cited

U.S. PATENT DOCUMENTS

| | | |
|---|---|---|
| 4,907,845 A | 3/1990 | Wood |
| 5,844,488 A | 12/1998 | Musick |

(Continued)

*Primary Examiner* — Jennifer L Norton
(74) *Attorney, Agent, or Firm* — Meister Seelig & Fein LLP; Seth H. Ostrow, Esq.

(57) ABSTRACT

A method and system for patient monitoring, the system comprising a surveillance camera configured to generate a plurality of frames showing an area in which a patient in a bed is being monitored, and a computer system comprising memory and logic circuitry configured to determine bed rails positions of the bed, identify a position of the patient, and generate signals that control the bed rails of a bed based on the bed rails positions and the position of the patient.

18 Claims, 6 Drawing Sheets

(51) Int. Cl.
*H04N 7/18* (2006.01)
*H04N 5/33* (2006.01)
*G16H 40/63* (2018.01)
*A61G 7/057* (2006.01)
*A61G 7/005* (2006.01)
*G08B 3/10* (2006.01)

(56) References Cited

U.S. PATENT DOCUMENTS

| | | |
|---|---|---|
| 6,544,200 B1 | 4/2003 | Smith et al. |
| 6,765,489 B1 | 7/2004 | Ketelhohn |
| 8,620,625 B2 | 12/2013 | Sing et al. |
| 8,675,920 B2 | 3/2014 | Hanson et al. |
| 8,907,287 B2 | 12/2014 | Vanderpohl |
| 9,072,929 B1 | 7/2015 | Rush et al. |
| 9,318,012 B2 | 4/2016 | Johnson et al. |
| 9,524,632 B2 | 12/2016 | Moore |
| 9,538,158 B1 | 1/2017 | Rush et al. |
| 9,597,016 B2 | 3/2017 | Stone et al. |
| 10,055,961 B1 | 8/2018 | Johnson et al. |
| 10,276,019 B2 | 4/2019 | Johnson et al. |
| 2003/0058111 A1 | 3/2003 | Lee et al. |
| 2003/0058341 A1 | 3/2003 | Brodsky et al. |
| 2004/0130452 A1 | 7/2004 | Cherubini |
| 2007/0132597 A1 | 6/2007 | Rodgers |
| 2008/0074270 A1 | 3/2008 | Ashwood-Smith et al. |
| 2008/0228039 A1 | 9/2008 | Huseth et al. |
| 2009/0063183 A1* | 3/2009 | McNeely ............ G16H 40/63 705/2 |
| 2009/0278934 A1 | 11/2009 | Ecker et al. |
| 2012/0029879 A1* | 2/2012 | Sing ............... A61B 5/1121 702/189 |
| 2012/0138801 A1 | 6/2012 | Vanderpohl |
| 2012/0140068 A1 | 6/2012 | Monroe et al. |
| 2014/0022081 A1* | 1/2014 | Ribble ............ A61B 5/6892 340/573.4 |
| 2014/0254579 A1 | 9/2014 | Huber et al. |
| 2014/0266669 A1 | 9/2014 | Fadell et al. |
| 2014/0267718 A1 | 9/2014 | Govro et al. |
| 2014/0288714 A1 | 9/2014 | Poviet |
| 2014/0313340 A1 | 10/2014 | Ecker et al. |
| 2015/0109442 A1* | 4/2015 | Derenne ............ G06F 19/00 348/143 |
| 2015/0199892 A1 | 7/2015 | Johnson et al. |
| 2015/0244993 A1* | 8/2015 | Greco ............... G16H 40/67 348/143 |
| 2016/0377704 A1 | 12/2016 | Harash et al. |
| 2017/0061763 A1 | 3/2017 | Hanson et al. |
| 2017/0108236 A1 | 4/2017 | Guan et al. |
| 2017/0155877 A1 | 6/2017 | Johnson et al. |
| 2017/0345275 A1* | 11/2017 | Ribble ............ G08B 21/0461 |
| 2017/0352240 A1 | 12/2017 | Carlton-Foss |
| 2020/0228755 A1* | 7/2020 | Greco ............... G16H 40/67 |

* cited by examiner

SYSTEMS AND METHODS FOR MONITORING AND CONTROLLING BED FUNCTIONS

CROSS REFERENCE TO RELATED APPLICATION

This application claims the priority of U.S. Provisional Application No. 62/723,193, entitled "SYSTEMS AND METHODS FOR MONITORING AND CONTROLLING BED FUNCTIONS," filed on Aug. 27, 2018, the disclosure of which is hereby incorporated by reference in its entirety.

The present application is related to the following patents and applications, which are assigned to the assignee of the present invention:
  a. U.S. Pat. No. 8,675,059, filed Jul. 29, 2010, entitled "System and method for using a video monitoring system to prevent and manage decubitus ulcers in patients,"
  b. U.S. Pat. No. 9,041,810, filed Jul. 1, 2014, entitled "System and method for predicting patient falls,"
  c. U.S. Pat. No. 9,311,540, filed May 6, 2008, entitled "System and method for predicting patient falls,"
  d. U.S. application Ser. No. 14/188,396, filed Feb. 24, 2014, entitled "System and method for using a video monitoring system to prevent and manage decubitus ulcers in patients,"
  e. U.S. Pat. No. 9,579,047, filed Mar. 14, 2014, entitled "Systems and methods for dynamically identifying a patient support surface and patient monitoring,"
  f. U.S. Pat. No. 9,635,320, filed May 12, 2015, entitled "Electronic Patient Sitter Management System and Method for Implementing,"
  g. U.S. application Ser. No. 15/332,283, filed Oct. 24, 2016, filed Oct. 22, 2015, entitled "PATIENT VIDEO MONITORING SYSTEMS AND METHODS FOR THERMAL DETECTION OF LIQUIDS," and
  h. U.S. application Ser. No. 15/364,872, filed Nov. 20, 2016, entitled "SYSTEM AND METHOD FOR PREDICTING PATIENT FALLS," the disclosure of which are hereby incorporated by reference in their entirety.

The above identified patents and applications are incorporated by reference herein in their entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

Field of the Invention

This application generally relates to patient bed monitoring, and in particular, using detection algorithms to perform automated adjustments of a patient's bed.

Description of the Related Art

There are significant safety concerns for hospital and nursing home patients, especially elderly patients, associated with falling out of a bed. Patient falls are among the most common occurrences reported in hospitals and are a leading cause of death in people of age 65 or older. Of those who fall, as many as half may suffer moderate to severe injuries that reduce mobility and independence, and increase the risk of premature death. One approach to addressing the problem is by the use of bed rails. The use of bed rails primarily protects an occupant of a bed from leaving or falling out of the bed, thus preventing injury. Such devices are often comprised of parallel guard rails or side panels that are affixed parallel to the direction the bed.

SUMMARY OF THE INVENTION

The present invention provides methods and systems for patient monitoring. According to one embodiment, the system comprises a surveillance camera configured to generate a plurality of frames showing an area in which a patient in a bed is being monitored, and a computer system comprising memory and logic circuitry configured to determine bed rails positions of the bed, identify a position of the patient, and generate signals that control the bed rails of a bed based on the bed rails positions and the position of the patient.

The system may further comprise the computer system configured to transmit the signals to the bed. In another embodiment, the system may further comprise the computer system configured to determine that the bed rails are in a lowered position, and generating a signal to raise the bed rails based on the determination of the bed rails in the lowered position. In yet another embodiment, the system may further comprise the computer system configured to determine that the bed rails are in a raised position and generating a signal to lower the bed rails based on a determination of a need for the patient to exit the bed. The surveillance camera may include at least one of image, depth, and thermal sensors. The system may further comprise the computer system configured to trigger an alarm based on whether the bed rails positions should be down or up.

The computer system may be configured to generate signals that control the bed rails of the bed to fold one or more of the bed rails. In another embodiment, the computer system may be configured to generate signals that lower the bed rails based on a signal or detection of a caregiver tending to the patient. The computer system may also be configured to analyze portions of sequential images from the plurality of frames for changes in an area of the bed that correlates to patient movements that are precursors to a fall and generate a signal that raises the bed rails based on a determination of patient fall risk according to the analysis.

According to another embodiment, the system comprises a surveillance camera configured to generate a plurality of frames showing an area in which a patient in a bed is being monitored, and a computer system comprising memory and logic circuitry configured to identify a position of the patient, determine a condition of the patient based on the position of the patient in relation to the bed, and generate signals that controls functions of the bed based on the position of the patient and the condition of the patient.

The functions of the bed may include at least one of bed rail control, bed movement control, and mattress inflation. According to another embodiment, the functions of the bed include at least one of mattress elevation, head or footrest movement, mattress tilting, mattress reclination, and mattress folding. The surveillance camera may include at least one of image, depth, and thermal sensors. The system may further comprise the computer system configured to determine the condition of the patient based on a heat signature of the patient suggesting a potential pressure ulcer in a given location. In one embodiment, the computer system may be configured to remotely manage positions of the bed to manage pressure ulcers.

The computer system may be configured to lift or inflate a mattress of the bed to alleviate pressure on the potential pressure ulcer. In another embodiment, the computer system may be configured to remotely manage positions of the bed to facilitate telemedicine. The bed may include a fluidized mattress. The computer system may also be configured to adjust fluid in the fluidized mattress based on the determined condition of the patient. The surveillance camera comprises a multispectral or thermographic camera that is capable of producing thermal images using infrared, or other non-visible or visible spectral, radiation.

BRIEF DESCRIPTION OF THE DRAWINGS

The invention is illustrated in the figures of the accompanying drawings which are meant to be exemplary and not limiting, in which like references are intended to refer to like or corresponding parts.

DETAILED DESCRIPTION OF THE INVENTION

Figure 1:
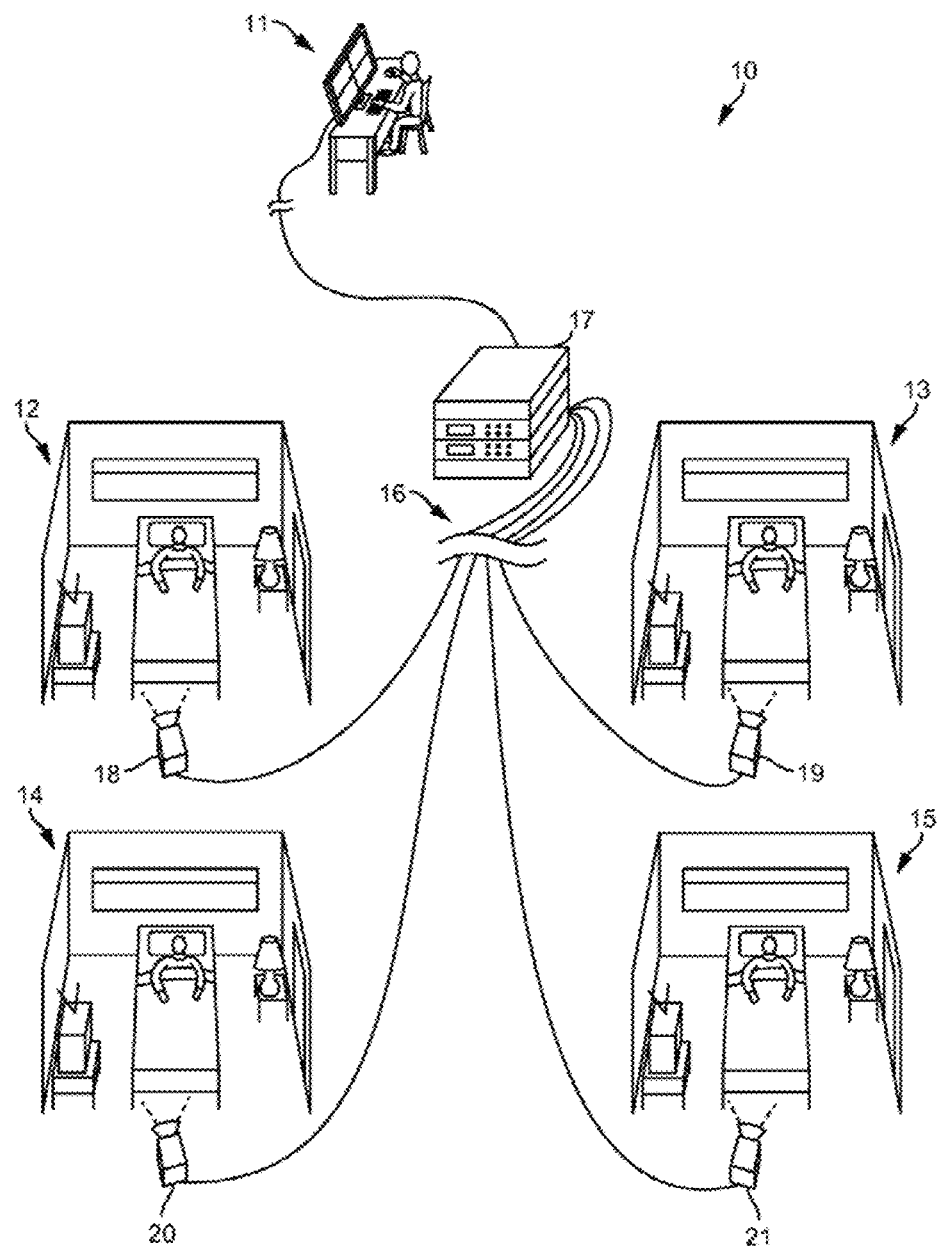
FIG. 1 illustrates a monitoring system according to an embodiment of the present invention.

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein; example embodiments are provided merely to be illustrative. It is to be understood that other embodiments may be utilized and structural changes may be made without departing from the scope of the present invention. Likewise, a reasonably broad scope for claimed or covered subject matter is intended. Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Various embodiments of the present disclosure concern video monitoring using multispectral and/or thermal sensors, object recognition, and imaging to detect patient events related to patient positioning and safety. Such events can concern situations in which a patient is at increased risk or otherwise is in need of intervention. Patient events can include patient bed activity, repositioning (e.g., for telemedicine consultation), and turning (e.g., to prevent pressure ulcers) among various other events. Thermal imaging, also known as thermography, is a technique for producing an image of invisible infrared light emitted by objects with the use of a thermal imaging camera. Multispectral imaging is a superset of thermal imaging and may be defined as technique for capturing image data at specific frequencies across the electromagnetic spectrum. A thermal and/or multispectral imaging camera is operable to produce an image showing the temperature differences of a surface. Images from the thermal or multispectral imaging camera may then be interpreted to detect, for example, liquids or potential pressure ulcers based on pre-defined heat signatures. Multispectral and thermal sensors and imaging may be incorporated into an health care facility's (HCF) monitoring system for identifying the patient events, monitoring them with surveillance audio/video ("A/V") data, alerting HCF staff of the patient events, and saving the surveillance A/V files to a storage device, along with corresponding identification data, for future retrieval.

Moreover, as will be discussed below, embodiments of the present monitoring system operates autonomously, without manual intervention. Using the exemplary monitoring system, the workload on the HCF staff can be significantly and immediately reduced through the implementation of a semi-autonomous patient monitoring system by using and analyzing video surveillance data in accordance with exemplary embodiments of the present invention. Here, the aim is to reduce the overall workload on the HCF staff professionals, while simultaneously creating a succinct video record of patient events by using multispectral and/or thermal imaging techniques with the video monitoring system. The presently described video monitoring system and method for detecting liquids in patient areas greatly reduces the amount of manual intervention required from an attending HCF staff member by automatically detecting the presence and volume of certain liquids. Additionally, the video record may be automatically annotated with relevant patient event information, timestamps, HCF staff comments and verifications and archived to locations secure from unauthorized alterations. These processes run largely in the background until and unless the system determines that intervention by the HCF staff is warranted.

FIG. 1 is a schematic diagram of a patient monitoring system 10. The patient monitoring system 10 can allow a healthcare professional to monitor multiple patient areas 12-15 from a monitoring station 11 via a computing system 17. The monitoring station 11 can comprise a user interface, which can include a screen and an input. The screen can display images of the patient areas 12-15, indications of one or more states of the patients being monitored, patient data, and/or other information. In some embodiments, the components of the monitoring station 11 are portable such that the monitoring station 11 can move with the healthcare processional.

While four patient areas 12-15 are shown in FIG. 1, any number of patient areas can be monitored at the monitoring station 11 via the computing system 17. The monitoring station 11 can be remote from the patient areas 12-15. For example, the monitoring station 11 can be on the same or different floor as the patient area 12-15, in the same or different building as the patient area 12-15, or located in a geographically different location as the patient area 12-15. Furthermore, the patient areas 12-15 can be remote from each other. The computing system 17 can be in one particular location or the components of the computing system 17 can be distributed amongst multiple locations. The computing system 17 can be at the monitoring station 11 or can be remote from the monitoring station 11 and/or the patient areas 12-15.

As shown in FIG. 1, a plurality of cameras 18-21 can be respectively positioned to view and generate frames of the plurality of patient areas 12-15. Information concerning the frames, such as analog or digital encodings of the frames, can be transmitted from the plurality of cameras 18-21 along data channels 16 to the computing system 17. In some cases, the computing system 17 is a single unit, such as a server, a personal computer (e.g., a desktop computer or a laptop computer), or a mobile computing device (e.g., smart phone, tablets, etc.). In some cases, the computing system 17 is distributed amongst several units, such as one or more personal computers, one or more mobile computing devices, one or more servers, circuitry within one or more of the cameras 18-21, and/or other computing devices. In some cases, the computing system 17 is part of a cloud computing network. The data channels 16 can be wired lines of a network (e.g., a local area network) and/or wireless channels (e.g., Wi-Fi or cellular network). The network may be any suitable type of network allowing transport of data communications across thereof. In other embodiments, the network may be the Internet, following known Internet protocols for data communication, or any other communication network, such as any wide area network (WAN) connection, or any combination thereof.

Each of the plurality of cameras 18-21 can generate a chronological series of frames (e.g., as images). The plurality of cameras 18-21 can be analog or digital cameras. Each of the plurality of cameras 18-21 can capture a sequence of frames at a predetermined frame rate, such as six, eight, sixteen, twenty-four, or some other number of frames per second. The resolution of digital cameras is usually defined by the number of pixels both horizontally and vertically (such as 640×480) or as a total number of pixels in the image (such as 1.4 mega pixels), while the resolution of analog video cameras is typically defined by the number of television lines. Analog frames can be converted to digital frames by analog-to-digital conversion circuitry (e.g., as part of the computing system 17 and/or the plurality of cameras 18-21). The plurality of cameras 18-21 can have infrared illumination or night vision capabilities for operating in low light conditions. According to one embodiment, the plurality of cameras 18-21 may include a multispectral or thermographic camera (or thermal imaging camera) capable of producing a thermal image of objects using infrared, or other non-visible or visible spectral, radiation.

Figure 2:
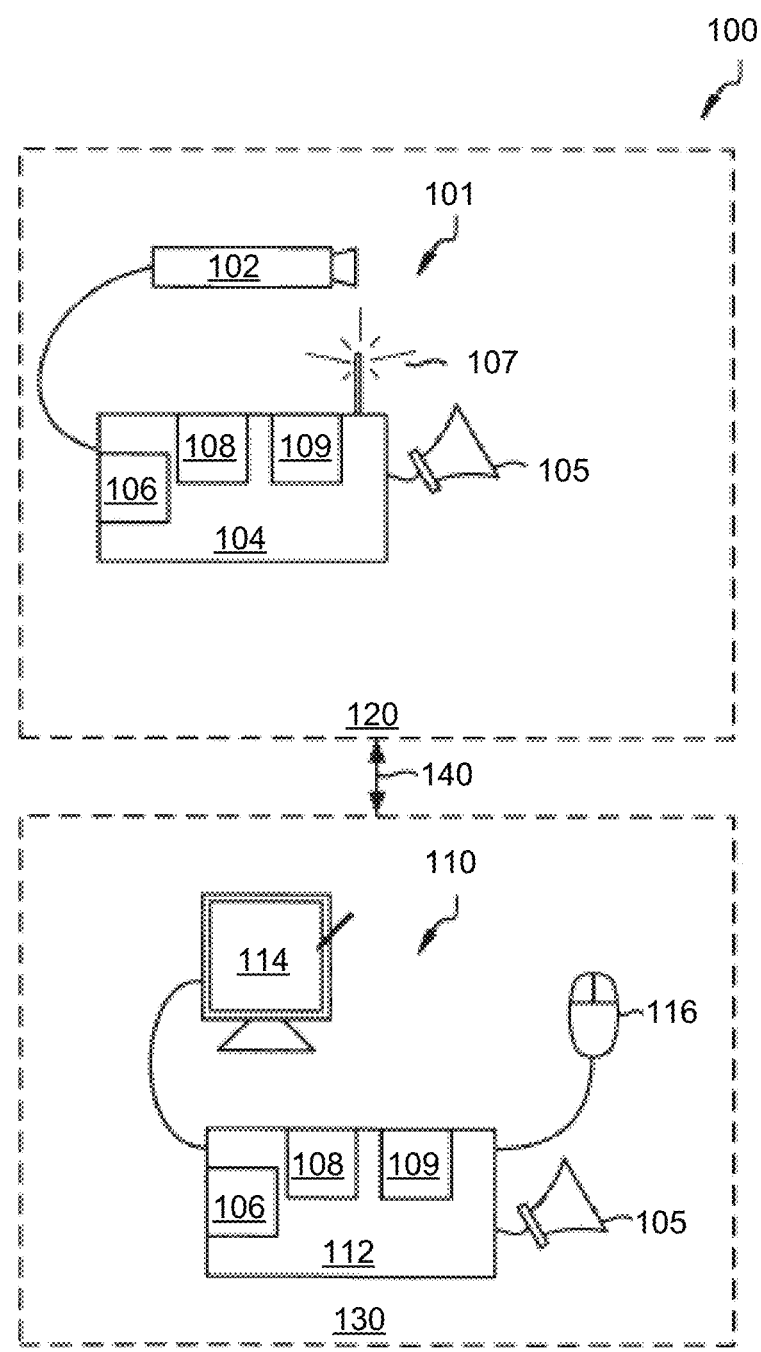
FIG. 2 illustrates a patient monitoring system according to an embodiment of the present invention.

FIG. 2 illustrates a diagram of a patient monitoring system in accordance with exemplary embodiments of the present invention. The depicted patient monitoring system 100 includes patient monitoring device 101 and nurse monitor device 110. Patient monitoring device 101 captures video images of a portion of the patient's room 120 via camera 102, which is coupled to control device 104. Camera 102 may be at least of medium quality, produce a stable video output of 300 lines of resolution or greater and have infrared illumination or quasi night vision for operating in extremely low light conditions. Additionally, video camera 102 may have a relatively fast shutter speed to capture relatively fast movements without blurring at frame rates of 20 fps or above.

The camera 102 can include optical components containing a lens, a filter, and/or other components for capturing and conditioning the light of the patient area. The camera 102 can further include a sensor for converting light from the optical components into electronic signals. Different types of sensors can be used depending on whether the camera is analog (e.g., generating analog video) or digital (e.g., generating discrete digital frames). For example, the camera 102 may include any singular or combination of an image sensor (e.g., a camera capable of video or still imagery), depth, and thermal sensors. The sensor can include a charge-coupled device (CCD), a complementary metal-oxide-semiconductor (CMOS), or a specialized thermal imaging focal plane array (FPA) image sensing device.

The camera can further include a processor and memory. The processor can perform various computing functions, such as those described herein or otherwise useful for operating the camera 102. The memory can be a non-transient computer readable storage medium (e.g., random access memory or flash) for storing program instructions and/or frames. For example, the processor can be configured to execute program instructions stored on the memory for controlling the camera 102 in converting visible or non-visible light from a patient area view into digital signals with the sensor, storing the digital signals on the memory as frame data, transferring the frame data to the control device 104, and/or performing any other function. The camera processor may perform various signal conditioning and/or image processing on the frames. The camera processor may also include a dedicated video processor for image processing. Although not illustrated, the camera 102 can further include a network interface controller and a power supply. The camera 102 may also include a user interface which can include user controls and/or an audible alarm.

Control device 104 processes the video images received from camera 102 in accordance with the novel methodology discussed below. As such, control device 104 includes processor 106, memory 108 and optional video processor 109. Control device 104 may be a special purpose device configured specifically for patient monitoring, such as the set-top control. In either case, memory 108 includes both ROM and RAM type as necessary for storing and executing bed rail control program instructions and a high capacity memory, such as a hard drive for storing large sequences of video image frames.

Additionally, control device 104 may be fitted with a high capacity flash memory for temporarily storing temporal image frames during image processing and/or prior to more permanent storage on a hard drive or at a network location. Optional video processor 109 may be a dedicated image processor under the control of an application routine executing on processor 106, or may be logic operating in processor 106. Control device 104 may comprise other components as necessary, such as network controllers, a display device and display controllers, user interface, etc.

Under fall prevention routines, video processor 109 may analyze portions of sequential images for changes in a particular area of a bed which correlate to patient movements that are precursors to a fall. Additionally, processor 109 may detect if bed rails on the bed are up or down, using object recognition and similar technologies. As such, the video processor 109 or processor 106 may communicate with the patient's bed (e.g., to an adjustment mechanism and/or control circuit of the bed) to adjust bed rail heights. The rails can be raised or lowered automatically based on the detection of rail position and other conditions such as a timer or a patient's need to get up or be prevented from falling out of the bed.

The patient monitoring system may also be used with specialized beds, such as air fluidized therapy mattresses or others, which move air or a fluid around to prevent bedsores. Under bedsore prevention routines, video processor 109 may analyze the positioning or movement of the patient on the bed, including how long a patient has been in one position. Alternatively, the video processor may be coupled to a thermal camera to detect the patient's heat signature suggesting a potential pressure ulcer in a given location. The video processor 109 or processor 106 may automatically move the air/fluid around in the mattress or adjust the fluid in the mattress to compensate based on the detection of video processor 109.

An alarm may also be generated based on the detections to alert healthcare providers. Patient monitoring device 101 may be coupled to nurse monitor device 110 located in nurse's station 130 via distribution network 140, for transmitting surveillance images of the patient's room and fall state information to nurse monitor device 110. Optionally, audible alarm 105 may be provided for alerting healthcare professionals that control device 104 has detected that the patient is at risk of falling.

Nurse monitor device 110 may be structurally similar to control device 104 and may be used to set up the fall prediction routines running at control device 104 and used to monitor fall state information and surveillance video provided by patient monitoring device 101. Optimally, nurse monitor device 110 is connected to a plurality of patient monitoring devices that are located in each of the patient rooms being monitored at the nurse station. Frames of the surveillance video may be automatically annotated with relevant patient event information, timestamps, HCF staff comments and verifications and archived to locations secure from unauthorized alterations. Nurse monitor device 110 includes computer 112 coupled to display 114. Computer 112 may be a personal computer, laptop, net computer, or other net appliance capable of processing the information stream. Computer 112 further comprises processor 106, memory 108 and optional video processor 109, as in control device 104, however these components function quite differently.

According to another embodiment, use of one or more sensors (e.g., image/thermal/depth), such as camera 102, in conjunction with a bed with remote controllable features can enable remote health care provides to reposition patients for telemedicine consultation. For example, information from one or more sensors may be used to detect a position and condition of a patient. Depending on the position and condition, a remote medical professional can use the sensor (s) to observe and remotely control the bed to manipulate the position of patient (e.g., raising/lower, tilting, and reclining of the bed).

In setup phase, a healthcare professional may be graphically or visually presented with views of a patient room setting on display 114 and allowed to graphically define areas of high risk for a patient fall, such as the patient bed, chair, shower, tub, toilet or doorways. Graphic objects corresponding to the patient room setting may be manipulated on display 114 by user gestures using resident touch screen capabilities or the user gestures may be entered onto a display space using mouse 116 or other type user interface through a screen pointer (not shown). Exemplary patient rooms from a viewpoint perspective of a video image are described more fully with respect to FIGS. 4A and 4B of commonly-owned U.S. Pat. No. 9,041,810, the description of which is incorporated herein by reference. Setup information provided by the healthcare professional corresponding to the patient room setting may be passed on to patient monitoring device 101 which monitors the selected area for motion predictive of a movement that is a precursor to a patient fall. When patient monitoring device 101 detects that the patient is at high risk of falling, the fall state may be immediately transmitted to nurse monitor device 110, which prioritizes the information over any other routine currently running as an alarm. This can be accompanied by an audible alarm signal (via audible alarm 105). The healthcare provider can then take immediate response action to prevent a patient fall.

In accordance with other exemplary embodiments of the present invention, patient monitoring device 101 may operate independently, as a self-contained, standalone device. In that case, patient monitoring device 101 may be configured with a display screen and user interface for performing setup tasks. Audible alarm 105 may not be optional. In accordance with still another exemplary embodiment, patient monitoring device 101 may comprise only video camera 102, which is coupled to nurse monitor device 110 at a remote location. In operation, camera 102 transmits a stream of images to nurse monitor device 110 for video processing for fall prediction. It should be appreciated, however, that often high volume traffic on distribution networks, such as sequences of video images, experience lag time between image capture and receipt of the images at the remote location. To avoid undesirable consequences associated with lag, the distribution network bandwidth should be sufficiently wide such that no lag time occurs, or a dedicated video path be created between nurse monitor device 110 and patient monitoring device 101. Often, neither option is practical and therefore, the video processing functionality may be located proximate to video camera 102 in order to abate any undesirable lag time associated with transmitting the images to a remote location.

Figure 3:
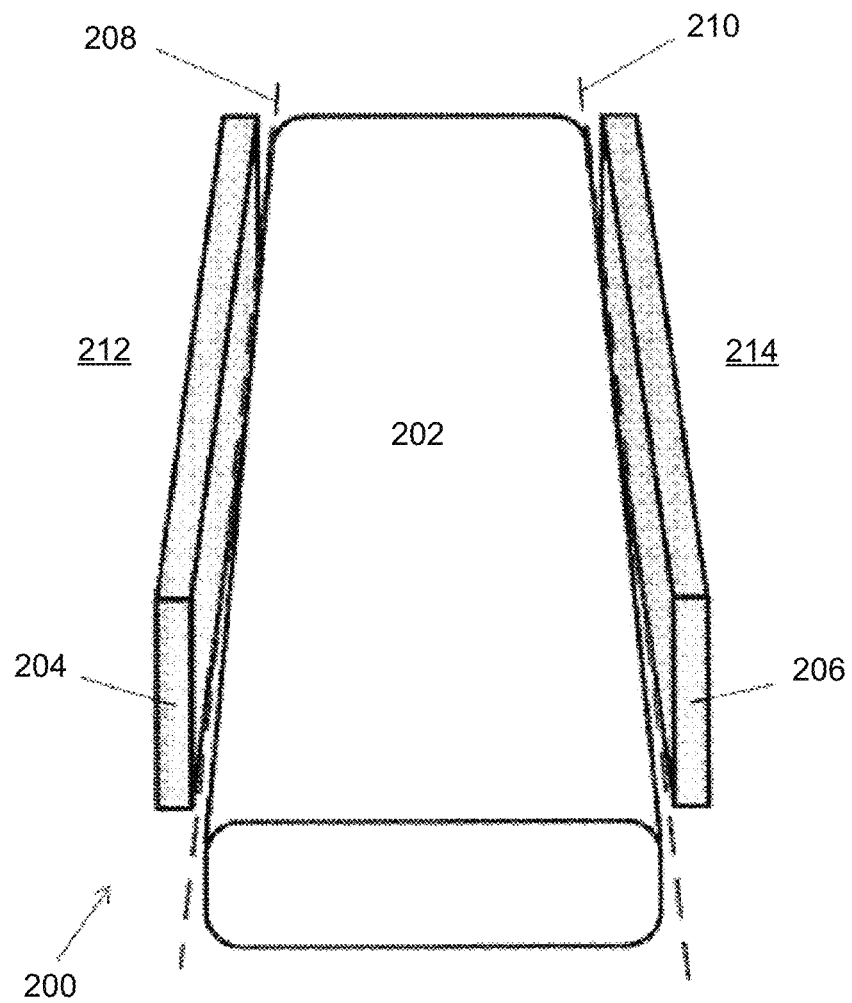
FIG. 3 illustrates an exemplary patient bed according to an embodiment of the present invention.

Referring now to FIG. 3, presents a block diagram of an embodiment of a bed 200 that may be used in and/or with some embodiments of the present systems and methods. The bed 200 may be, for example, a hospital or patient bed of conventional, therapeutic, and/or smart variant. In the embodiment shown, bed 200 includes a mattress 202, a right-side rail 204, and a left-side rail 206. A right-side rail boundary 208 is depicted by a dashed line lying along the edge of mattress 202 nearest the right-side rail. A left-side rail boundary 210 is depicted by a dashed line lying along the edge of the edge of mattress 202 nearest the left-side rail. Left and right-side rail boundaries 208 and 210 are shown as examples to illustrate one embodiment of the present systems and methods.

Additional and/or alternative boundaries (e.g., foot-end and/or head-end edges of mattress 202) may also be defined in relation to a bed. In embodiments of the present invention, boundaries may be three-dimensional surfaces (e.g., planar or curved surfaces), collections of points defining vertices of a three-dimensional space, and/or three-dimensional spaces defined by combinations of surfaces and vertices. Combinations of any these different types of boundaries may be used simultaneously. Boundaries 208 and 210 may define out-of-bed regions 212 and 214, respectively, on the right side of boundary 208 and left side of boundary 210. Out-of-bed region 212 includes a portion of bed 200 that includes right-side rail 204, and out-of-bed region 214 includes a portion of bed 200 that includes left-side rail 206.

Bed 200, for example, may be equipped with one or more sets of controls that allow the patient and/or hospital staff to adjust the bed. The controls may elevate or lower mattress 202, raise or lower the head or foot of the mattress, fold the mattress into a seat, inflate the mattress, deflate the mattress, and/or raise, lower, or fold one or both of side-rails 204 and 206. Many combinations of the aforementioned adjustments as well as additional adjustments may be included in the bed. For example, certain adjustable beds are specifically designed for the treatment of certain medical conditions and may be capable of complex adjustments particular to that condition.

Figure 4:
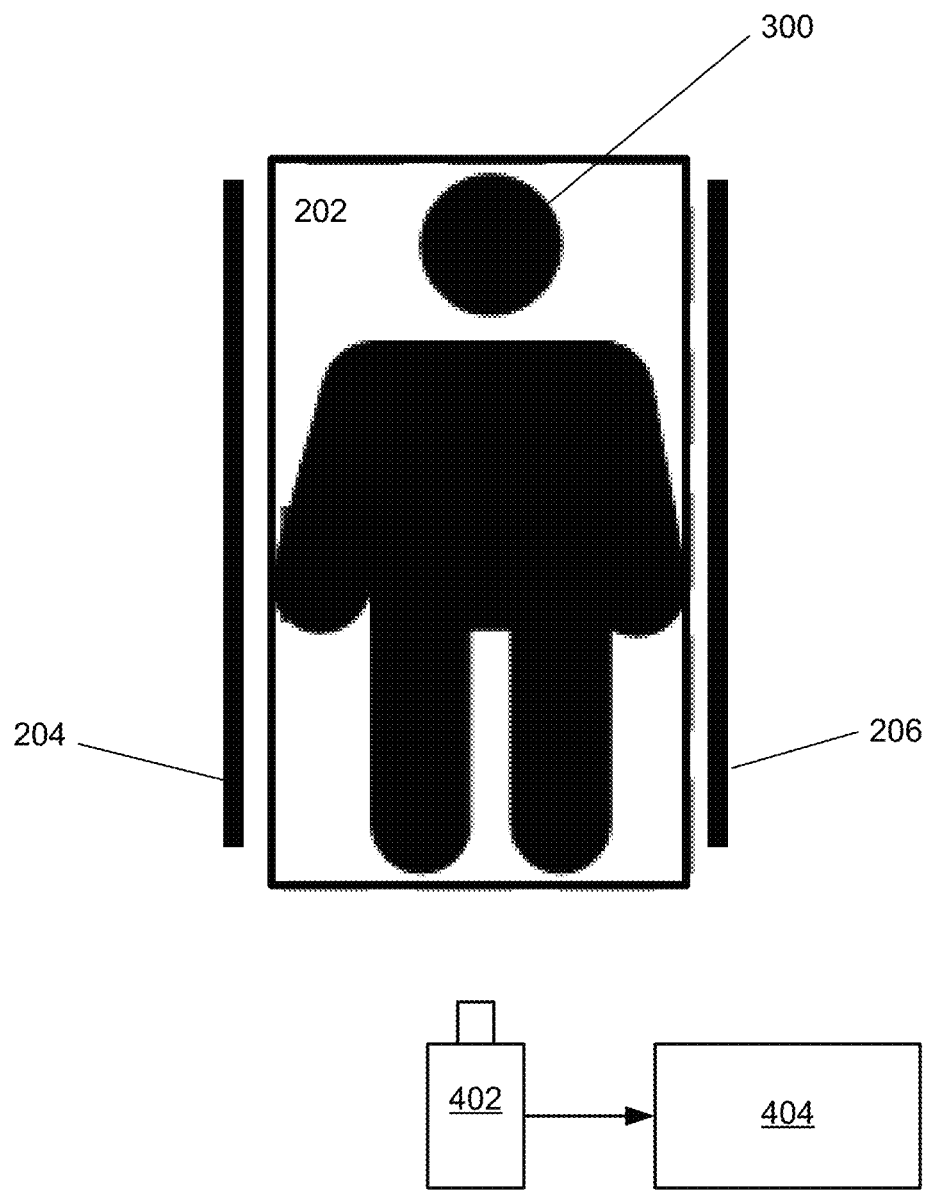
FIG. 4 illustrates a bed and monitoring system according to an embodiment of the present invention.

FIG. 4 depicts an embodiment of a patient monitoring system. The system comprises bed 200 including a patient 300 shown lying on mattress 202 between right and left-side rails 204 and 206. In the embodiment shown, the system comprises a camera 402 that is configured to generate video information. Camera 402 is positioned and/or otherwise configured to have a field of view such that sensor can generate video information of the bed and/or patient. The camera 402 is communicatively coupled to controller 404. Controller 404 may be located either within a local vicinity of camera 402 or remotely, for example, a nurse monitoring device located in a centralized location such as a nurse's station.

Camera 402 and controller 404 may be used to detect, for example, pressure ulcer risk, or if side rails 204 and 206 are up or down using object recognition and thermal imaging techniques. Controller 404 is capable of communicating with bed 200 to perform a plurality of bed control functions including bed rail control, bed movement control, and mattress inflation. The controller 404 may include artificial intelligence or logic trained by machine learning to automatically carry out bed control functions in response to certain detected conditions.

According to one embodiment, controller 404 may raise or lower side rails 204 and/or 206 automatically based on the detection and other conditions such as a timer or a patient's need to get up or be prevented from falling out of the bed. Side rails 204 and 206 may be raised to reduce the risk of injury to patients from falling from a bed while unsupervised. Additionally, side rails 204 and/or 206 may be lowered based on a detection of patient 300 needing to get up or based on a signal or detection of caregivers attempting to tend to the patient 300. In another embodiment, controller 404 may variably lift or inflate the mattress of a bed to alleviate pressure on certain body parts to prevent bed sores or ulcers according to a timer, bed rolling schedule routine, or detected conditions of a patient.

Figure 5:
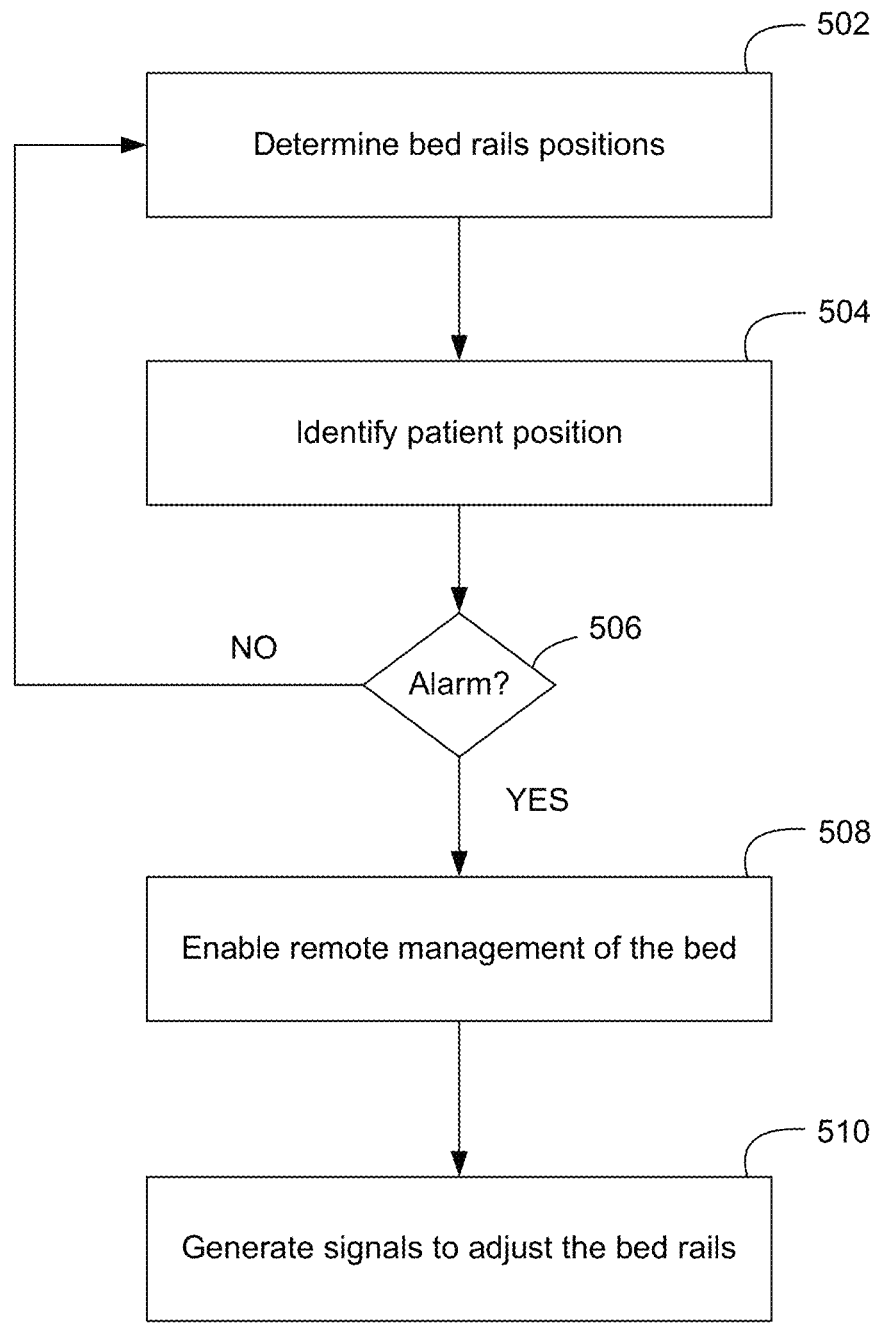
FIG. 5 illustrates a flowchart of a method for controlling bed rails according to an embodiment of the present invention.

FIG. 5 presents a flowchart of a method for controlling bed rails according to an embodiment of the present invention. Bed rails positions are determined, step 502. Determining bed rails positions may include receiving information from sensors and/or cameras to detect if physical bed rails on a bed of a patient are raised or lowered. A patient position is identified, step 504. The position of the patient on the bed may be identified using the information from the sensors and/or cameras to determine whether the patient is in danger or in a compromised situation. According to another embodiment, identifying the patient position may further include determining the presence of a caregiver. The presence of the caregiver may obviate the need to raise an alarm if the bed rails are in a lowered position (e.g., the caregiver is tending to the patient).

Depending on the position of the bed rails, position of the patient, and known information (such as fall risk), an alarm can be raised, step 506. According to one embodiment, in the event that the bed rails are up or if a caregiver is present, no alarm is triggered, and the system proceeds to step 502. Otherwise, if the bed rails are down or lowered, the alarm may be triggered, and remote management of the bed is enabled, step 508. The remote management may comprise, for example, any smart bed action or response. Signals to adjust the bed rails are generated, step 510. The signals may be generated automatically by and communicated from, for example, a controller at a remote monitoring station, to the patient's bed where the bed rails may be automatically raised. The system may also determine whether the position of the patient renders it unsafe to adjust the bed rails (e.g., the patient's limbs are obstructing the bed rails). Alternatively, a determination of the patient's need to leave the bed may also be detected from the patient position, such as the patient sitting up, or the patient pressing a button. In such an instance, the system may generate signals to the patient's bed to lower the bed rails to allow a patient to get out of bed.

Figure 6:
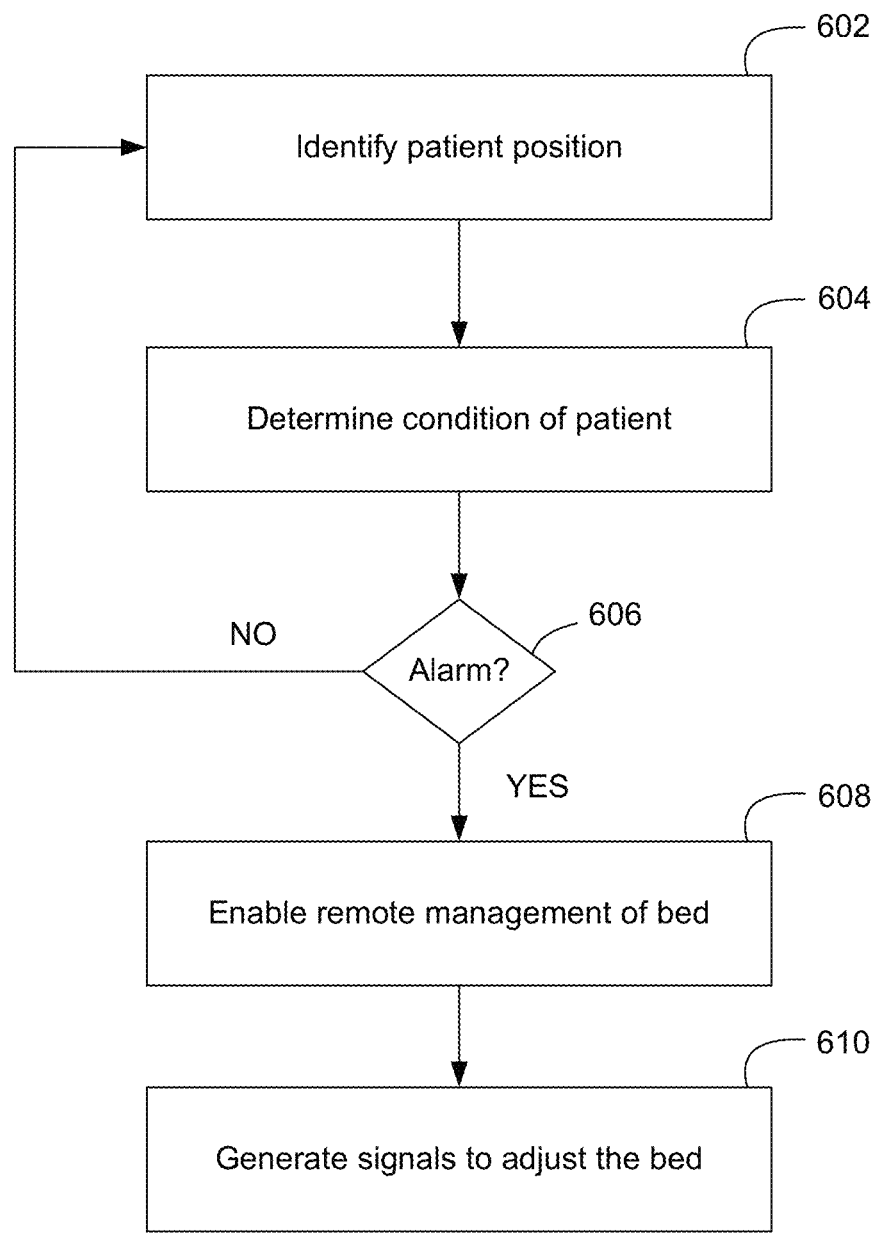
FIG. 6 illustrates a flowchart of a method for pressure ulcer prevention according to an embodiment of the present invention.

FIG. 6 presents a flowchart of a method for pressure ulcer prevention according to an embodiment of the present invention. A patient position is identified, step 602. Identifying the patient position may include receiving information from sensors and/or cameras to detect body orientations of the patient. A condition of the patient is determined, step 604. The condition of the patient may be determined based on, for example, known medical information (such as mobility of the patient), how long the patient has been in the same or similar position, whether the patient is in a correct position according to a turning schedule, or whether the patient is in a harmful position. Determining the condition of the patient may further include detecting the patient's heat signature suggesting a potential pressure ulcer in a given location. Alternatively, the condition of the patient may be determined using any one or more of image, depth, and thermal sensors to identify characteristics of the patient and the bed or in relation to the bed to determine if a patient needs to be repositioned.

Based on the patient position and the condition of the patient, the system determines whether to raise an alarm, step 606. If the patient position and condition of the patient is acceptable, the system proceeds to step 602. Otherwise, a determination that the condition of the patient is not acceptable can trigger the alarm advance the system to proceed to enable remote management of the bed, step 608. Certain actions or functions of the bed may be enabled for remote control depending on the position of the patient, time in same/similar position, and known medical information.

Signals to adjust the bed are generated, step 610. Depending on the position of the patient, time in same/similar position, and known medical information (such as mobility of patient), the system may automatically generate and transmit signals to the bed to position the patient by adjusting mattress inflation pressures or firmness. The signals may be generated and communicated from, for example, a controller at a remote monitoring station.

FIGS. 1 through 6 are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

It should be understood that various aspects of the embodiments of the present invention could be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps). In software implementations, computer software (e.g., programs or other instructions) and/or data is stored on a machine readable medium as part of a computer program product, and is loaded into a computer system or other device or machine via a removable storage drive, hard drive, or communications interface. Computer programs (also called computer control logic or computer-readable program code) are stored in a main and/or secondary memory, and executed by one or more processors (controllers, or the like) to cause the one or more processors to perform the functions of the invention as described herein. In this document, the terms "machine readable medium," "computer-readable medium," "computer program medium," and "computer usable medium" are used to generally refer to media such as a random access memory (RAM); a read only memory (ROM); a removable storage unit (e.g., a magnetic or optical disc, flash memory device, or the like); a hard disk; or the like.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

What is claimed is:

1. A system for preventing patient falls, the system comprising:
    a surveillance camera configured to generate a plurality of frames showing an area in which a patient in a bed is being monitored; and
    a computer system comprising memory and logic circuitry configured to:
    determine bed rails positions of the bed;
    identify a position of the patient;
    generate signals that control the bed rails of a bed based on the bed rails positions and the position of the patient;
    transmit the generated signals to the bed; and
    control the bed rails with the generated signals.

2. The system of claim 1 further comprising the computer system configured to:
    determine that the bed rails are in a lowered position; and
    generate a signal that raises the bed rails based on the determination of the bed rails in the lowered position.

3. The system of claim 1 further comprising the computer system configured to:
    determine that the bed rails are in a raised position; and
    generate a signal that lowers the bed rails based on a determination of a need for the patient to exit the bed.

4. The system of claim 1 wherein the surveillance camera includes at least one of image, depth, and thermal sensors.

5. The system of claim 1 further comprising the computer system configured to trigger an alarm based on whether the bed rails positions should be down or up.

6. The system of claim 1 further comprising the computer system configured to generate signals that control the bed rails of the bed to fold one or more of the bed rails.

7. The system of claim 1 further comprising the computer system configured to generate signals that lower the bed rails based on a signal or detection of a caregiver tending to the patient.

8. The system of claim 1 further comprising the computer system configured to:
    analyze portions of sequential images from the plurality of frames for changes in an area of the bed that correlates to patient movements that are precursors to a fall; and
    generate a signal that raises the bed rails based on a determination of patient fall risk according to the analysis.

9. A method for preventing patient falls, the method comprising:
    receiving, by a computer system, information including a plurality of frames from a surveillance camera, the plurality of frames showing an area in which a patient in a bed is being monitored;
    determining, by the computer system, bed rails positions of the bed based on the information;
    identifying, by the computer system, a position of the patient based on the information;
    generating, by the computer system, signals that control the bed rails of the bed based on the bed rails positions and the position of the patient
    transmitting the generated signals to the bed; and
    controlling the bed rails with the generated signals.

10. The method of claim 9 further comprising:
    determining that the bed rails are in a lowered position; and
    generating a signal that raises the bed rails based on the determination of the bed rails in the lowered position.

11. The method of claim 9 further comprising:
    determining that the bed rails are in a raised position; and
    generating a signal that lowers the bed rails based on a determination of a need for the patient to exit the bed.

12. The method of claim 9 wherein the surveillance camera includes at least one of image, depth, and thermal sensors.

13. The method of claim 9 further comprising triggering an alarm based on whether the bed rails positions should be down or up.

14. The method of claim 9 further comprising generating signals that control the bed rails of the bed to fold one or more of the bed rails.

15. The method of claim 9 further comprising generating signals that lower the bed rails based on a signal or detection of a caregiver tending to the patient.

16. The method of claim 9 further comprising:
analyzing portions of sequential images from the plurality of frames for changes in an area of the bed that correlates to patient movements that are precursors to a fall; and
generating a signal that raises the bed rails based on a determination of patient fall risk according to the analysis.

17. Non-transitory computer-readable media comprising program code that when executed by a programmable processor causes execution of a method for preventing patient falls, the computer-readable media comprising:
computer program code for receiving information including a plurality of frames from a surveillance camera, the plurality of frames showing an area in which a patient in a bed is being monitored;
computer program code for determining bed rails positions of the bed based on the information;
computer program code for identifying a position of the patient based on the information;
computer program code for generating signals that control the bed rails of the bed based on the bed rails positions and the position of the patient;
computer program code for transmitting the generated signals to the bed; and
controlling the bed rails with the generated signals.

18. The non-transitory computer-readable media of claim 17 further comprising:
computer program code for analyzing portions of sequential images from the plurality of frames for changes in an area of the bed that correlates to patient movements that are precursors to a fall; and
computer program code for generating a signal that raises the bed rails based on a determination of patient fall risk according to the analysis.

\* \* \* \* \*